(12) United States Patent
Sumi et al.

(10) Patent No.: US 6,342,367 B1
(45) Date of Patent: Jan. 29, 2002

(54) METHOD FOR THE PREPARATION OF CHONDROITIN SULFATE COMPOUNDS

(75) Inventors: Toshihisa Sumi, Tosu; Hideki Ohba, Kitakyushu; Toru Ikegami, Tosu; Masao Shibata, Ogoori; Tsuyoshi Sakaki, Tosu; Imre Sallay, Tosu; Sung Soo Park, Tosu, all of (JP)

(73) Assignee: Japan as represented by Secretary of Agency of Industrial Science and Technology, Tokyo-to (JP)

( * ) Notice: Subject to any disclaimer, the term of this patent is extended or adjusted under 35 U.S.C. 154(b) by 0 days.

(21) Appl. No.: 09/513,191

(22) Filed: Feb. 25, 2000

(30) Foreign Application Priority Data

Nov. 18, 1999 (JP) .......................................... 11-328355

(51) Int. Cl.$^7$ .......................... C12P 21/06; C12P 19/00; C07K 1/00; A23D 1/00; C07H 11/00
(52) U.S. Cl. ...................... 435/68.1; 435/72; 435/100; 435/101; 435/267; 435/274; 530/412; 530/416; 530/417; 530/418; 530/424; 530/427; 536/118
(58) Field of Search .......................... 435/68.1, 72, 100, 435/101, 267, 274; 530/412, 416, 417, 418, 424, 427; 536/118

(56) References Cited

U.S. PATENT DOCUMENTS 4,302,577 A * 11/1981 Rucker ........................ 536/118
5,718,723 A * 2/1998 Matsuda et al. ................ 623/1
6,093,563 A * 7/2000 Bennett et al. .............. 435/232

FOREIGN PATENT DOCUMENTS

WO    WO 99/40941    *  8/1999
WO    WO 00/35959    *  6/2000

OTHER PUBLICATIONS

Tam et al., *Infection and Immunity*, vol. 47, No. 2, pp. 508–513, Feb. 1985.*
Catalog of *SIGMA—ALDRICH*, pp. 253–255, 2000.*
*Chemical Abstract*, vol. 121, pp. 1174–1175, Ref. #109685V (Chinese Patent No. 1,080,929), 1994.*
Griffin, *Trans. Am. Fish. Soc.*, vol. 120, No. 3, pp. 391–395, 1991.*

* cited by examiner

Primary Examiner—Christopher S. F. Low
Assistant Examiner—Abdel A. Mohamed
(74) Attorney, Agent, or Firm—Wenderoth, Lind & Ponack, LLP

(57) ABSTRACT

Disclosed is an economical method for the preparation of chondroitin sulfates A and C useful as an effective ingredient of medicaments from fish scales as a waste material discharged from fishery in large quantities. Fish scales are enzymatically decomposed in an aqueous medium in the presence of a protease to isolate the chondroitin sulfate compounds and by-product polypeptides followed by removal of the by-product polypeptides from the aqueous solution by a cation-exchange treatment and then the aqueous solution of the chondroitin sulfate compounds is subjected to fractional precipitation by the addition of ethyl alcohol as the precipitant.

7 Claims, No Drawings

METHOD FOR THE PREPARATION OF CHONDROITIN SULFATE COMPOUNDS

BACKGROUND OF THE INVENTION

The present invention relates to a novel and economical method for the preparation of chondroitin sulfate compounds. More particularly, the invention relates to a method for the preparation of chondroitin sulfate compounds including chondroitin sulfate A and chondroitin sulfate C having usefulness as an effective ingredient in eye lotions and therapeutic medicaments for neuralgia and arthralgia by using an inexpensive raw material available in large quantities.

Chondroitin sulfate is a generic name for a class of compounds known as a kind of typical glycosaminoglycans widely distributing in nature as a constituent of cartilage tissues and connective tissues of a great variety of animals. These compounds each have a polymeric structure consisting mainly of 40 to 100 times repetition of the disaccharide units expressed by the structural formula, the subscript n being the number of repetition of the disaccharide units:

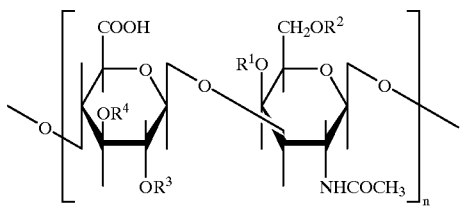

which can be classified into several types depending on the combinations and bonding positions of the substituents $R^1$ to $R^4$ including chondroitin sulfate A when $R^1$ is $SO_3H$ and $R^2$, $R^3$ and $R^4$ are each a hydrogen atom, i.e. chondroitin-4-sulfate, chondroitin sulfate C when $R^2$ is SOH and $R^1$, $R^3$ and $R^4$ are each a hydrogen atom, i.e. chondroitin-6 sulfate, chondroitin sulfate D when $R^2$ and $R^3$ are each $SO_3H$ and $R^1$ and $R^4$ are each a hydrogen atom, chondroitin sulfate E when $R^1$ and $R^2$ are each $SO_3H$ and $R^3$ and $R^4$ are each a hydrogen atom, chondroitin sulfate K when $R^1$ and $R^4$ are each $SO_3H$ and $R^2$ and $R^3$ are each a hydrogen atom and chondroitin sulfate B, i.e. dermatan sulfate, when most of the D-glucuronic acids are 5-epimerized into L-iduronic acid of which $R^1$ is a sulfate group.

Among these chondroitin sulfate compounds, chondroitin sulfate A is prepared mainly from notochords of sturgeons or nasal cartilages of whales and chondroitin sulfate C is prepared mainly from cartilages of sharks as the respective starting raw materials. Availability of these raw materials, however, is limited and, in addition, the procedure for the preparation of the chondroitin sulfate compounds from these materials is relatively complicated not to be suitable for large-scale production of the products consequently with a high production cost.

SUMMARY OF THE INVENTION

The present invention accordingly has an object, in view of the above described problems in the conventional processes for the preparation of chondroitin sulfate compounds or, in particular, chondroitin sulfates A and C from raw materials of limited availability, to provide a novel and economical method suitable for large-scale preparation of these chondroitin sulfate compounds by a simple and convenient process from a raw material of good availability.

Thus, the method of the present invention for the preparation of chondroitin sulfate compounds or, in particular, chondroitin sulfate A and chondroitin sulfate C comprises the steps of:

(a) subjecting fish scales to an enzymatic solubilization treatment in an aqueous medium with a protease to give an aqueous solution of isolated chondroitin sulfate compounds containing polypeptides as a by-product;

(b) removing the by-product polypeptides from the aqueous solution obtained in step (a); and (c) subjecting the aqueous solution after removal of the polypeptides to fractional precipitation of the chondroitin sulfate compounds.

DETAILED DESCRIPTION OF THE PREFERRED EMBODIMENTS

The above described method of the present invention for the preparation of chondroitin sulfate compounds has been established as a result of the extensive investigations undertaken by the inventors including the screening tests to uncover raw materials of good availability from which the desired chondroitin sulfate compounds can be advantageously prepared arriving at an unexpected discovery that fish scales as an industrial waste material discharged from fishery in large quantities are suitable for the purpose.

Namely, the method of the present invention comprises simple steps of (a) enzymatic solubilization of fish scales to give an aqueous solution containing the isolated chondroitin sulfate compounds, (b) removal of the by-product polypeptides from the aqueous solution and (c) fractional precipitation of the chondroitin sulfate compounds contained in the aqueous solution.

The fish from which fish scales as the starting material of the inventive method are obtained can be any of freshwater fishes and saltwater fishes without particular limitations. Examples of freshwater fishes suitable for the purpose include carps, crucians, trouts, goldfishes and others. Examples of the saltwater fishes suitable for the purpose include sea breams, sea basses, salmons, herrings, etsu fish and others. Scales of these fishes can be used after merely removing filthy matters by washing with water. If necessary, the fish scales after washing with water are subjected to a heat treatment at a temperature of 120 to 130° C. for 5 to 30 minutes in. order to facilitate homogenization of the fish scales prior to step (a).

The solubilization treatment of fish scales as the starting material in step (a) of the inventive method is conducted by dispersing the fish scales as the starting material in a diluted aqueous solution of calcium acetate or, preferably, in an aqueous solution buffered with a tris hydrogen chloride buffer solution at a pH of 7.4 to 8.0 followed by homogenization with a homogenizer to give an aqueous suspension of the comminuted fish scales to which a protease is added to effect proteolytic decomposition of the fish scales. This proteolytic reaction is conducted preferably at a temperature of 30 to 40° C. and the reaction is completed usually within 5 hours to several days at this temperature.

This treatment has an effect to proteolytically decompose the proteinous material which combines with the chondroitin sulfate compounds in the fish scales to isolate polypeptides as a by-product which is dissolved in the aqueous medium together with the chondroitin sulfate compounds to form an aqueous solution.

In the next place, the aqueous solution still containing insoluble matters is subjected to filtration or centrifugation for removal of the insoluble matters to give a clear solution from which the polypeptides as a by-product are removed in step (b) of the inventive method. This treatment of step (b) can be conducted advantageously by bringing the aqueous solution into contact with a cation-exchange resin in the $H^+$-form. Though optional, this ion-exchange treatment can be preceded by evaporation of a part of water from the aqueous solution and subjecting the thus concentrated aqueous solution to dialysis-against distilled water.

In step (c) of the inventive method, the thus obtained aqueous solution containing the isolated chondroitin sulfate compounds is subjected to fractional precipitation of the chondroitin sulfate compounds. Thus, the aqueous solution is admixed step-wise with ethyl alcohol and the precipitated matters obtained for the respective ethyl alcohol concentrations of the precipitation medium are collected as the fractions consisting of different chondroitin sulfate compounds which precipitate when the step-wise increasing ethyl alcohol concentration has reached the precipitation point of the individual compounds.

Identification of the thus isolated chondroitin sulfate compounds can be conducted by subjecting the respective products to hydrolysis with a digestive enzyme and detecting the thus produced saccharides by making comparison with an authentic sample of the chondroitin sulfate compound. In particular, this identification procedure is undertaken by hydrolyzing the sample of chondroitin sulfate with chondroitinase and developing-the thus obtained solution in thin-layer chromatography, referred to as TLC hereinafter, followed by color development of the spots of the bands for the unsaturated disaccharides with a diphenylamine reagent to make comparison for coincidence of the band distribution with that obtained from an authentic sample.

The conclusion obtained by such an identification test of the products obtained by the inventive method is that the chondroitin sulfate compounds obtained from fish scales are chondroitin sulfate A and chondroitin sulfate C.

In the following, the method of the present invention is described in more detail by way of Examples.

EXAMPLE 1.

Scales of carps in an amount of 60 g were thoroughly washed with water-and subjected to a heat treatment at 120° C. for 20 minutes. Thereafter, the fish scales after the heat treatment were added to 300 ml of a 0.05M tris hydrogen chloride buffer solution at a pH of 7.8 containing 0.02M of calcium acetate together with 300 mg of a protease (Actinase E, a product by Kaken Seiyaku Co.) followed by homogenization with a homogenizer to give a uniform suspension of the comminuted fish scales. This aqueous suspension was incubated at 37° C. for 3 days so that the fish scales were completely solubilized followed by a heat treatment of the reaction mixture at 100° C. for 5 minutes to deactivate the enzyme.

After centrifugation at 20000 rpm for 40 minutes to settle the insoluble matters in the reaction mixture, the clear supernatant was subjected to evaporation of a part of water to give a 100 ml volume of a concentrated solution which was dialyzed overnight against distilled water. The aqueous solution after the dialysis treatment was passed through an ion-exchange column of 50 mm inner diameter and 50 mm depth filled with a cation-exchange resin (Dowex 50-x8, a product by Dow Chemical Co.) in the $H^+$-form to remove the polypeptides produced by the proteolysis and contained in the aqueous solution. The effluent solution from the column was neutralized with sodium hydroxide and then freeze-dried to give 330 mg of a freeze-dried material.

The thus obtained freeze-dried material was dissolved in 50 ml of a 0.5M aqueous solution of sodium acetate and the pH value of the solution was brought to 4.5 by the addition of acetic acid. The solution was then admixed with ethyl alcohol portion-wise to increase the concentration of ethyl alcohol step-wise and the precipitates formed in the mixture at the respective ethyl alcohol concentrations were collected.

The precipitates from each of the fractions were admixed with 2N hydrochloric acid in a 1000 w/v times amount and the mixture was heated at 100° C. for 20 hours to effect hydrolysis of the chondroitin sulfate into saccharides. The saccharide solution was analyzed for the composition of saccharides by using a saccharide analyzer (Model DX-500, manufactured by Dionex Co.). The results are shown in Table 1 below together with the yields of the precipitates from the respective fractions, in which the names of various saccharides are abridged as follows.

| Fuc | fucose |
| Gal | galactose |
| GlcUA | glucuronic acid |
| GalNAc | N-acetyl galactosamine |
| GlcNAc | N-acetyl glucosamine |
| NeuAc | N-acetyl neuraminic acid |
| NeuGc | N-glycolyl neuraminic acid |

TABLE 1

| Ethyl alcohol concentration, % | Yields of precipitates, mg | Composition of saccharides, µg/mg | | | | | | |
|---|---|---|---|---|---|---|---|---|
| | | Fuc | Gal | GlcUA | GalNAc | GlcNAc | NeuAc | NeuGc |
| 0–40 | 5.0 | 11.15 | 43.54 | 13.38 | 47.46 | 18.23 | 2.69 | 0.00 |
| 40–50 | 49.0 | 11.67 | 28.23 | 129.41 | 157.37 | 29.62 | 1.18 | 0.00 |
| 50–60 | 4.0 | 14.01 | 33.75 | 32.50 | 64.74 | 27.76 | 3.49 | 0.00 |

TABLE 1-continued

| Ethyl alcohol concentration, % | Yields of precipitates, mg | Composition of saccharides, μg/mg | | | | | | |
|---|---|---|---|---|---|---|---|---|
| | | Fuc | Gal | GlcUA | GalNAc | GlcNAc | NeuAc | NeuGc |
| 60–70 | 6.0 | 17.50 | 69.02 | 6.79 | 60.09 | 35.09 | 41.52 | 12.22 |
| 70< | 70.0 | 3.43 | 20.47 | 0.00 | 7.33 | 13.49 | 39.53 | 15.63 |

As is understood from this table, the precipitates obtained from the fraction of 40–50% ethyl alcohol concentration contained GlcUA and GalNAc in higher contents than in the other fractions and the molar ratio of GlcUA and GalNAc was about 1:1. Iduronic acid as a constituent saccharide of chondroitin sulfate B was not detected in any of the fractions.

A 75 μg portion of the precipitates obtained from the fraction of 40–50% ethyl alcohol concentration and each a 50 μg portion of authentic samples of chondroitin sulfate A and chondroitin sulfate C of the SSG grade (each a product by Biochemical Industry Co.), referred to as ChsA and ChsC, respectively, hereinafter, were dissolved each in 100 μl of a 0.025M sodium acetate buffer solution having a pH of 5.0 and each solution was admixed with a solution prepared by dissolving 0.02 unit of chondroitinase (Earthro II, a product by Biochemical Industry Co.) in 2 μl of the same buffer solution followed by incubation of the mixtures at 37° C. for 20 hours to effect the enzymatic reaction. Thereafter, the reaction mixtures were each admixed with 300 μl of ethyl alcohol to deactivate the enzyme followed by centrifugation to settle the insoluble matters.

The supernatants from centrifugation were, after evaporation of a part of water, subjected to thin-layer chromatographic analysis by using a Silica Gel 60 TLC Plate (a product by Merck Co.) with a 2:1:1 by volume mixture of n-butyl alcohol, acetic acid and distilled water as the developer. A diphenylamine reagent was used as the color developer for the unsaturated disaccharides formed by the enzymatic reaction with the chondroitinase.

The TLC spot diagram obtained from the fraction corresponding to 40–50% ethyl alcohol concentration indicated to two spots of unsaturated disaccharides. The mobility of each of these spots was in good coincidence with that for the disaccharides obtained from authentic samples of ChsA and ChsC.

EXAMPLE 2

The experimental procedure was substantially the-same as in Example 1 excepting for the replacement of 60 g of carp scales as the starting material with 142 g of scales of red sea breams to obtain 95 mg as a total of precipitates by fractionation with ethyl alcohol as the precipitant. Table 2 below shows the results of the saccharide analysis of the precipitates from each of the five fractions.

TABLE 2

| Ethyl alcohol concentration, % | Yields of precipitates, mg | Composition of saccharides, μg/mg | | | | | | |
|---|---|---|---|---|---|---|---|---|
| | | Fuc | Gal | GlcUA | GalNAc | GlcNAc | NeuAc | NeuGc |
| 0–40 | 6.1 | 5.30 | 167.44 | 26.53 | 181.04 | 29.13 | 23.07 | 0.00 |
| 40–50 | 23.3 | 2.40 | 102.91 | 197.65 | 264.73 | 83.68 | 11.25 | 7.85 |
| 50–60 | 11.7 | 0.44 | 53.58 | 25.50 | 57.11 | 33.75 | 58.51 | 55.34 |
| 60–70 | 5.2 | 4.10 | 4.77 | 6.66 | 93.67 | 0.00 | 99.41 | 29.32 |
| 70< | 48.7 | 9.34 | 7.00 | 0.00 | 226.40 | 0.00 | 153.95 | 0.00 |

EXAMPLE 3

The experimental procedure was substantially the same as in Example 1 excepting for the replacement of 60 g of carp scales as the starting-material with 26 g of scales of etsu fish to obtain 20.8 mg as a total of precipitates by fractionation with ethyl alcohol as the precipitant. Table 3 below shows the results of the saccharide analysis of the precipitates from each of the five fractions.

TABLE 3

| Ethyl alcohol concentration, % | Yields of precipitates, mg | Composition of saccharides, μg/mg | | | | | | |
|---|---|---|---|---|---|---|---|---|
| | | Fuc | Gal | GlcUA | GalNAc | GlcNAc | NeuAc | NeuGc |
| 0–40 | 2.4 | 19.40 | 22.13 | 87.23 | 94.63 | 0.00 | 24.49 | 0.00 |
| 50–60 | 3.4 | 18.03 | 6.74 | 2.73 | 82.91 | 0.00 | 44.60 | 0.00 |

TABLE 3-continued

| Ethyl alcohol concentration, % | Yields of precipitates, mg | Composition of saccharides, μg/mg | | | | | | |
|---|---|---|---|---|---|---|---|---|
| | | Fuc | Gal | GlcUA | GalNAc | GlcNAc | NeuAc | NeuGc |
| 60–70 | 2.6 | 23.07 | 6.75 | 3.00 | 65.98 | 0.00 | 23.46 | 9.72 |
| 70< | 12.4 | 12.93 | 8.40 | 1.55 | 138.72 | 0.00 | 113.39 | 25.76 |

EXAMPLE 4

The experimental procedure was substantially the same as in Example 1 excepting for the replacement of 60 g of carp scales as the starting material with 23 g of scales of sea basses to obtain 11.0 mg as a total of precipitates by fractionation with ethyl alcohol as the precipitant. Table 4 below shows the results of the saccharide analysis of the precipitates from each of the five fractions.

TABLE 4

| Ethyl alcohol concentration, % | Yields of precipitates, mg | Composition of saccharides, μg/mg | | | | | | |
|---|---|---|---|---|---|---|---|---|
| | | Fuc | Gal | GlcUA | GalNAc | GlcNAc | NeuAc | NeuGc |
| 0–40 | 1.4 | 4.91 | 11.01 | 67.92 | 82.36 | 0.00 | 11.57 | 0.00 |
| 50–60 | 1.7 | 1.93 | 131.13 | 2.63 | 14.25 | 0.00 | 15.03 | 0.00 |
| 60–70 | 1.2 | 6.19 | 8.14 | 0.00 | 27.09 | 0.00 | 18.95 | 0.00 |
| 70< | 6.7 | 7.62 | 4.66 | 0.00 | 175.68 | 0.00 | 112.81 | 12.59 |

As is understood from Tables 2 to 4, the chondroitin sulfate compounds obtained by the protease treatment of fish scales include chondroitin sulfate A and chondroitin sulfate C while chondroitin sulfate B is not included therein irrespective of the kind of the fishes.

What is claimed is:

1. A method for the preparation of chondroitin sulfate A and chondroitin sulfate C as a mixture which comprises the steps of:

(a) subjecting fish scales to an enzymatic solubilization treatment in an aqueous medium with a protease to give an aqueous solution of chondroitin sulfate A and chondroitin sulfate C containing polypeptides as a by-product, and (b) removing the by-product polypeptides from the aqueous solution of chondroitin sulfate A and chondroitin sulfate C obtained in step (a) by bringing the aqueous solution into contact with a cation-exchange resin in the H$^+$-form.

2. The method for the preparation of chondroitin sulfate A and chondroitin sulfate C as claimed in claim 1 in which the cation-exchange treatment of the aqueous solution is preceded by a dialysis treatment of the aqueous solution against water.

3. A method for the preparation of chondroitin sulfate A and chondroitin sulfate C as a mixture which comprises the steps of:

(a) subjecting fish scales to an enzymatic solubilization treatment in an aqueous medium with a protease to give an aqueous solution of chondroitin sulfate A and chondroitin sulfate C containing polypeptides as a by-product;

(b) removing the by-product polypeptides from the aqueous solution of chondroitin sulfate A and chondroitin sulfate C obtained in step (a) by bringing the aqueous solution into contact with a cation-exchange resin in the H$^+$-form; and (c) subjecting the aqueous solution after removal of the polypeptides in step (b) to fractional precipitation of the chondroitin sulfate A and chondroitin sulfate C for the removal of by-products.

4. The method for the preparation of chondrotin sulfate A and chondroitin sulfate C as claimed in claim 3 in which step (a) is preceded by a step of a heat treatment of the fish scales at a temperature in the range from 120 to 130° C. for 5 to 30 minutes.

5. The method for the preparation of chondroitin sulfate A and chondroitin sulfate C as claimed in claim 3 which the solubilization treatment of fish scales is conducted by heating the fish scales in an aqueous medium containing a protease at a temperature in the range from 30 to 40° C. for at least 5 hours.

6. The method for the preparation of chondroitin sulfate A and chondroitin sulfate C as claimed in claim 3 in which the fractional precipitation of chondroitin sulfate A and chondroitin sulfate C is conducted by the addition of ethyl alcohol step-wise to the aqueous solution.

7. The method for the preparation of chondroitin sulfate A and chondroitin sulfate C as claimed in claim 3 in which the cation-exchange treatment of the aqueous solution is preceded by a dialysis treatment of the aqueous solution against water.

* * * * *